United States Patent [19]

Ries

[11] 4,389,487

[45] Jun. 21, 1983

[54] PROCESS FOR THE PREPARATION OF A COLLAGEN PRODUCT FOR MEDICAL AND COSMETIC PURPOSES

[75] Inventor: Peter E. Ries, Reinach, Switzerland

[73] Assignee: Pentapharm A.G., Basel, Switzerland

[21] Appl. No.: 269,023

[22] PCT Filed: Sep. 17, 1980

[86] PCT No.: PCT/CH80/00107

§ 371 Date: Jun. 8, 1981

§ 102(e) Date: May 29, 1981

[87] PCT Pub. No.: WO81/00963

PCT Pub. Date: Apr. 16, 1981

[30] Foreign Application Priority Data

Oct. 8, 1979 [CH] Switzerland .................. 9030/79

[51] Int. Cl.³ .................................... C07G 7/00
[52] U.S. Cl. .................................... 435/273; 426/32; 604/368; 128/DIG. 8
[58] Field of Search .................. 435/68, 273; 426/32; 128/296, DIG. 8

[56] References Cited

U.S. PATENT DOCUMENTS

| | | | |
|---|---|---|---|
| 3,303,038 | 2/1967 | Klevens | 426/32 X |
| 3,664,844 | 5/1972 | Miller | 426/32 |
| 4,066,083 | 1/1978 | Ries | 435/273 X |

FOREIGN PATENT DOCUMENTS

| | | | |
|---|---|---|---|
| 585232 | 10/1959 | Canada | 435/273 |
| 665262 | 6/1963 | Canada | 435/273 |
| 673203 | 6/1939 | Fed. Rep. of Germany . | |
| 1692548 | 8/1971 | Fed. Rep. of Germany . | |
| 2625289 | 12/1976 | Fed. Rep. of Germany . | |
| 2108068 | 5/1972 | France . | |
| 2369329 | 5/1978 | France . | |
| 1144552 | 3/1969 | United Kingdom . | |

*Primary Examiner*—Robert A. Yoncoskie
*Attorney, Agent, or Firm*—Pennie & Edmonds

[57] ABSTRACT

Process for the preparation of collagen products for medical and cosmetic purposes, wherein collagen products prepared according to the method described in U.S. Pat. No. 4,066,083 are subjected to an additional heat treatment or a treatment with gaseous hydrogen halide in order to improve the physicochemical and mechanical properties of the collagen product, in particular its absorption and mechanical strength.

7 Claims, No Drawings

PROCESS FOR THE PREPARATION OF A COLLAGEN PRODUCT FOR MEDICAL AND COSMETIC PURPOSES

TECHNICAL FIELD

The present invention relates to the preparation of a collagen product for medical and cosmetic purposes which has a felt-, sponge- or fleece-like structure and which has significantly improved physicochemical and mechanical properties (absorption, strength) as compared with known collagen products.

BACKGROUND ART

It is known practice to use collagen products prepared from animal tissues in medicine for treating wounds and for filling pathological cavities in bones. Collagen products of this type are described e.g. in the following patents: British Pat. No. 1,147,072, South African Pat. No. 6,705,871, U.S. Pat. No. 4,016,877, U.S. Pat. No. 3,823,212, U.S. Pat. No. 3,810,473 and U.S. Pat. No. 4,066,083 (P. Ries).

The process described in U.S. Pat. No. 4,066,083 comprises comminuting collagen-containing animal tissues at a temperature not exceeding 40° C., degreasing the resulting tissue pulp and simultaneously removing therefrom undesirable water-soluble non-collagen ballast substances by repeatedly treating the tissue pulp with about a five-fold volume, based on the pulp volume, of a 5 to 15% aqueous sodium chloride solution containing about 0.2 to 1 part by weight of sodium azide as a preserving agent per 1000 parts by weight of the said solution and 0.5 to 2% by weight of a non-ionic fat-dispersing wetting agent, washing the resulting fiber pulp with water or 0.1 to 0.5% aqueous formic, acetic or citric acid, digesting the fiber pulp for 8 to 48 hours at a pH of about 2.5 to 3.5 in a five-fold volume, based on the volume of the pulp, of 0.1 to 5% aqueous acetic acid containing about 1 part by weight of pepsin per 1000 parts by weight of the tissue used as the starting material in order to remove non-collagen type proteins and telopeptides, precipitating collagen from the resulting collagen suspension by the addition thereto of aqueous sodium chloride in such a quantity that the sodium chloride concentration of the suspension is about 3 to 5%, separating the precipitated collagen and desalting it by ultrafiltration, dialysis or washing with 60 to 75% aqueous ethyl alcohol, dissolving the desalted collagen in demineralized or distilled water containing up to 3% by weight of a strong organic acid in such a proportion that the concentration of collagen in the resulting solution corresponds to a dry residue of about 0.5 to 2% by weight, freeze-drying the collagen solution, and sterilizing the freeze-dried collagen product.

The collagen product obtained by this process possesses a number of advantageous properties which appear to make it particularly suitable as an auxiliary material in medicine, but has the disadvantage that it is slow in taking up aqueous solutions or body fluids and has insufficient mechanical strength in moist or wet condition.

DISCLOSURE OF THE INVENTION

Surprisingly, it was found that the physicochemical and mechanical properties of the collagen product could be substantially improved by treating the freeze-dried collagen product, before or after sterilization, with heat or gaseous hydrogen halide. The improved collagen product is even more suitable and easier to handle for medical purposes. Due to its improved physicochemical and mechanical properties, the new collagen product can also be used as a cosmetic mask for skin care.

According to the invention, the collagen product can be subjected, after freeze-drying, either before or after sterilization, to a heat treatment at temperatures of 80° to 150° C., preferably 100° to 130° C., for 15 minutes to 12 hours, preferably 1 to 6 hours, at normal pressure or in vacuo. The freeze-dried collagen product can also be subjected, before or after sterilization, to a treatment with gaseous hydrogen halide, preferably hydrogen chloride, for 1 to 60 minutes, preferably 5 minutes. As a result of these treatments, the absorption and the wet strength of the collagen product are increased. Simultaneously, a reduction in the number of germs in the collagen product is achieved. The collagen product treated in the manner described above takes up about 50 to 100 times its weight of water within 1 minute, whereas the collagen product prepared according to U.S. Pat. No. 4,066,083 without the additional treatment can take up no more than about 25 to 30 times its weight of water within 10 minutes. The collagen product prepared according to the invention has an increased mechanical strength, even after having taken up water or body fluids, so that it is easy to handle even in a wet condition.

BEST MODE FOR CARRYING OUT THE INVENTION

The starting material required for carrying out the process according to the invention can be prepared in the manner described below.

1 kg of bovine tendons was frozen at −10° to −20° C. and then finely comminuted by means of a high speed knife homogenizer. The temperature of the comminuted material was kept below 40° C. by adding pieces of ice. The viscous fibrous tissue pulp thus obtained was suspended, while vigorously stirring, in 5 liters of 10% aqueous sodium chloride solution containing 2.5 g of sodium azide and 50 ml of a 10% aqueous solution of the non-ionic wetting agent NP 55/52 (polyoxyethylene nonyl phenyl ether). The suspension was stirred for an additional 2 hours at room temperature and then centrifuged. The grayish or brownish turbid supernatant phase containing fats and undesirable water-soluble accompanying ballast substances was discarded. The residual white fiber pulp was further extracted twice in the same manner, except that 0.1 mole of disodium hydrogenophosphate was added to the extraction fluid.

Instead of bovine tendons, pig skin can be used as the starting material.

A degreased and extracted fibrous tissue pulp prepared from 1 kg of bovine tendons in the manner described above was suspended in 5 times its volume of 0.5 M acetic acid. To the suspension, a solution of 1 g of technical pepsin in 100 ml of 0.01 N HCl was added. The pH of the suspension was adjusted to 2.9 by means of HCl. The suspension, while repeatedly stirred, was digested for 48 hours. The viscous collagen solution was filtered on a suction filter G 1 in order to remove undigested residues. The collagen was precipitated from the suspension by the addition of 30% aqueous sodium hydroxide solution and separated by centrifugation. The collagen was purified by dissolution in 0.5 M acetic acid and precipitation by slowly adding 3% aqueous sodium chloride. The purified collagen was dissolved in 0.5 M acetic acid and diluted with water. The residual sodium chloride present in the collagen was removed by washing on an ultrafilter. The ultrafiltration was continued until no chloride ions were detectable in the eluate after addition of silver nitrate and the collagen concentration amounted to about 1%. The collagen solution was filtered and finally freeze-dried.

EXAMPLE 1

A collagen solution prepared according to the method described above was poured into a heat-resistant mold and freeze-dried in a freeze-dryer, with the temperature being increased to 98° C. toward the end of the freeze-drying and the drying process being continued for 6 hours at this temperature. After cooling and breaking of the vacuum, the dried collagen product was packed and sterilized by irradiation with γ-rays.

A collagen fleece prepared according to the method described above and having a size of about 60×35×7 mm and a weight of 220 mg takes up 15 ml of water within 42 seconds. In comparison, an untreated collagen fleece of the same size and weight takes 9 minutes to absorb only 5 ml of water. Upon wetting, the collagen fleece having not been subjected to heat treatment becomes pulpy-soft so that it cannot be handled anymore, whereas the heat-treated collagen fleece remains supple and, in wet condition, dimensionally stable and capable of being handled for at least ½ hour.

EXAMPLE 2

Before use, a freeze-dried collagen product prepared according to the method described above was heated at 100° C. for 1½ hours in a conventional electrically heated drying oven and, after cooling, tested for absorption, absorption velocity and mechanical wet strength as described in example 1. The product thus obtained had the same qualitatively improved properties as the product obtained according to example 1.

EXAMPLE 3

Equal quantities of a collagen solution prepared according to the method described above were poured into heat-resistant identical molds and freeze-dried to obtain collagen fleeces. Half of the fleeces were subjected to a heat treatment in the manner described in example 1. The treated and untreated fleeces were cut into 5 cm wide sample strips and moistened with 12 ml of water each. The wet tensile strengths of the samples were measured under the same conditions in a breaking apparatus. As demonstrated by the following table, the wet tensile strength of the treated collagen fleeces is significantly higher than that of the untreated fleeces. The fleeces which had been additionally treated for 6 hours at 90° C. broke only at a load of 60 to 92 g, whereas the untreated fleeces broke at a load of 14 to 22 g.

| Sample No. | Collagen Wet Tensile Strength | |
|---|---|---|
| | untreated | treated |
| 1 | load 22 g | load 92 g |
| 2 | load 14 g | load 60 g |
| 3 | load 14 g | load 64 g |
| 4 | load 14 g | load 82 g |
| 5 | load 18 g | load 72 g |
| 6 | load 18 g | load 66 g |
| 7 | load 18 g | load 76 g |
| 8 | load 20 g | load 66 g |
| ∅ = load 17.25 g | | ∅ = load 72.25 g |

The wet tensile strength was determined as follows. Sample strips of collagen fleece having a size of 11×5×0.7 cm were fixed between two 6 cm wide clamps placed at a distance of 10 cm. The central portion of the samples was previously moistened with 12 ml of distilled water. One of the clamps was fastened, whereas the other was pulled away at constant speed. The force applied to the collagen sample until breaking occurred was measured with a dynamometer.

EXAMPLE 4

Collagen fleece samples prepared according to the method described above and having a size of 5×11×0.7 mm were divided into two groups A and B, each comprising 10 fleeces. Group A was heated at 125° C. for 3 hours in a drying oven, whereas group B remained untreated. Subsequently the wet tensile strength of the samples was measured in the manner described in example 3.

| Sample No. | Group A | Group B |
|---|---|---|
| 1 | load 18 g | load 120 g |
| 2 | load 22 g | load 142 g |
| 3 | load 20 g | load 162 g |
| 4 | load 18 g | load 132 g |
| 5 | load 14 g | load 162 g |
| 6 | load 14 g | load 146 g |
| 7 | load 22 g | load 164 g |
| 8 | load 18 g | load 148 g |
| 9 | load 14 g | load 150 g |
| 10 | load 14 g | load 140 g |
| | ∅ = load 17.4 g | ∅ = load 146.6 g |

EXAMPLE 5

Samples weighing about 200 to 240 mg were cut from collagen fleeces prepared and heat-treated in the manner described in example 4. The samples were tested to determine their water absorption capacity. For this purpose, each sample was placed in a shallow polystyrene dish and moistened with 16 ml of water. After 1 minute, the polystyrene dishes were inclined by 45° in order to drain the excess of water not absorbed by the collagen fleece. The measured absorption of the heat-treated samples amounted to about 50 to 60 times their own weight, as demonstrated by the following table. After 24 hours, the wet collagen fleece samples were still dimensionally stable and capable of being handled.

| A Weight of Collagen | B Absorption without heat treatment | C Absorption after heat treatment at 125° C. for 3 hours | Quotient 1000 × C:A |
|---|---|---|---|
| 241 mg | 5.6 ml H$_2$O | 13.9 ml H$_2$O | 57.6 |
| 222 mg | 5.5 ml H$_2$O | 11.7 ml H$_2$O | 52.7 |
| 203 mg | 5.3 ml H$_2$O | 12.3 ml H$_2$O | 60.6 |
| 242 mg | 5.6 ml H$_2$O | 13.9 ml H$_2$O | 57.4 |

EXAMPLE 6

A collagen fleece prepared according to the method described above was enclosed in a desiccator containing a vessel with concentrated hydrochloric acid instead of a drying agent. The collagen fleece was allowed to stand in the hydrogen chloride atmosphere for 5 minutes, then taken out, allowed to stand in the air for 1 hour and eventually tested as to its absorption, velocity of absorption and mechanical wet tensile strength, as described in example 1. The collagen fleece thus treated had the same qualitatively improved properties as the product prepared according to example 1.

The obtained product was tested for wet tensile strength under the conditions set forth in example 3. The following values were obtained:

| Sample No. | Collagen Wet Tensile Strength | |
|---|---|---|
| | Untreated | Treated with HCl |
| 1 | load 20 g | load 76 g |
| 2 | load 18 g | load 70 g |
| 3 | load 14 g | load 72 g |
| 4 | load 18 g | load 60 g |
| average | load 17.5 g | load 69.5 g |

It had already been known to improve the physico-chemical properties of collagen or gelatin products in a chemical way, e.g. by cross-linking with aldehydes, in particular formaldehyde or glutaraldehyde. However, these methods of treatment have the disadvantage that the obtained products are resorbed very slowly or not at all by the body in medical implantations and, in addition, cause inflammations, defense reactions or the formation of giant foreign body cells. It was, therefore, totally unexpected and inexplicable that the physico-chemical properties of collagen products could be significantly improved by a simple heat or HCl treatment and that the thus treated products would not show the above-mentioned disadvantages in their medical application in the body. This was all the more surprising since, as is well known, collagen solutions are highly heat sensitive and must be treated at temperatures not exceeding 35° C.

I claim:

1. In a process for the preparation of collagen products for medical and cosmetic purposes comprising the steps of finely comminuting collagen-containing animal tissues at temperatures not exceeding 40° C., degreasing the resulting tissue pulp and simultaneously removing therefrom undesireable water-soluble non-collagen type ballast substances by repeatedly treating the said tissue pulp with about a five-fold volume, based on the pulp volume, of a 5 to 15% aqueous sodium chloride solution containing about 0.2 to 1 part by weight of sodium azide as a preserving agent per 1000 parts by weight of the said solution and 0.5 to 2% by weight of a non-ionic fat-dispersing wetting agent, washing the resulting fiber pulp with water or 0.1 to 0.5% aqueous formic, acetic or citric acid, digesting the fiber pulp for 8 to 48 hours at a pH of about 2.5 to 3.5 in a five-fold volume, based on the volume of the pulp, of 0.1 to b 5% aqueous acetic acid containing about 1 part by weight of pepsin per 1000 parts by weight of the tissue used as the starting material in order to remove non-collagen type proteins and telopeptides, precipitating collagen from the resulting collagen suspension by the addition thereto of aqueous sodium chloride in such a quantity that the sodium chloride concentration of the suspension is about 3 to 5%, separating the precipitated collagen and substantially desalting it by ultrafiltration, dialysis or washing with 60 to 75% aqueous ethyl alcohol so that the collagen concentration in the desalted solution is about 1%, dissolving the desalted collagen in demineralized or distilled water containing up to 3% by weight of a volatile strong organic acid in such a proportion that the concentration of collagen in the resulting solution corresponds to a dry residue of about 0.5 to 2% by weight, freeze-drying the collagen solution, and sterilizing the freeze-dried collagen product, the improvement comprising:

subjecting the collagen product to a heat treatment or a treatment with gaseous hydrogen halide after freeze-drying, before or after sterilization, for a time sufficient to impart increased absorption and wet strength to the collagen product.

2. The process according to claim 1 which comprises subjecting the freeze-dried collagen product to temperatures of 80° to 150° C. for ¼ to 12 hours and sterilizing the collagen product by irradiation.

3. The process according to claim 1 which comprises subjecting the freeze-dried collagen product to a hydrogen halide atmosphere for 1 to 60 minutes.

4. The process according to claim 1 which comprises using pig skin as the animal tissue.

5. The process according to claim 1 which comprises using bovine tendons as the animal tissue.

6. The process according to claim 1 which comprises subjecting the freeze-dried collagen product to a hydrogen chloride atmosphere for 1 to 60 minutes.

7. An improved collagen product, having a felt-, sponge- or fleece-like structure, obtained by the process according to one of claims 1, 2, 3, 4, 5 or 6, wherein the improvement comprises increased absorption and wet strength of the collagen product.

* * * * *